(12) United States Patent
Richard

(10) Patent No.: US 7,537,781 B2
(45) Date of Patent: May 26, 2009

(54) POLYMER-FILLER COMPOSITES FOR CONTROLLED DELIVERY OF THERAPEUTIC AGENTS FROM MEDICAL ARTICLES

(75) Inventor: Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 813 days.

(21) Appl. No.: 10/777,801

(22) Filed: Feb. 12, 2004

(65) Prior Publication Data
US 2005/0181014 A1   Aug. 18, 2005

(51) Int. Cl.
*A61F 2/82* (2006.01)

(52) U.S. Cl. .................. 424/425; 425/423; 425/424

(58) Field of Classification Search .............. None
See application file for complete search history.

(56) References Cited

U.S. PATENT DOCUMENTS

| | | | |
|---|---|---|---|
| 5,514,734 A | 5/1996 | Maxfield et al. | 523/204 |
| 5,698,624 A | 12/1997 | Beall et al. | 524/445 |
| 5,733,925 A | 3/1998 | Kunz et al. | 514/449 |
| 5,741,331 A | 4/1998 | Pinchuk | 623/11 |
| 6,057,396 A | 5/2000 | Lan et al. | 524/445 |
| 6,083,559 A | 7/2000 | Beall et al. | 427/220 |
| 6,087,016 A | 7/2000 | Feeney et al. | 428/454 |
| 6,126,734 A | 10/2000 | Beall et al. | 106/487 |
| 6,180,378 B1 | 1/2001 | Shen et al. | 435/176 |
| 6,232,389 B1 | 5/2001 | Feeney et al. | 524/450 |
| 6,399,690 B2 | 6/2002 | Lan et al. | 524/445 |
| 6,545,097 B2 | 4/2003 | Pincuk et al. | 525/240 |
| 2002/0107330 A1 | 8/2002 | Pinchuk et al. | 525/242 |
| 2002/0143094 A1 | 10/2002 | Conroy et al. | 524/445 |
| 2003/0039742 A1 | 2/2003 | Qiu et al. | 427/2.1 |
| 2003/0065355 A1 | 4/2003 | Weber | 606/200 |
| 2003/0093107 A1 | 5/2003 | Parsonage et al. | 606/194 |
| 2003/0125803 A1 | 7/2003 | Vallana et al. | 623/1.42 |
| 2003/0143350 A1 | 7/2003 | Jimenez | 428/35.2 |
| 2003/0144727 A1 | 7/2003 | Rosenthal et al. | 623/1.15 |
| 2003/0161866 A1 | 8/2003 | Kostyniak et al. | 424/449 |

OTHER PUBLICATIONS

Acquarulo Jr., Lawrence; O'Neil, Charles J.; "Enhancing Medical Device Performance with Nanocomposite Polymers". Medical Devicelink. May 2002. pp. 1-8. http://www.devicelink.com/mddi/archive/02/05/006.html.
"InMat-Technology". http://www.inmat.com/technology-tmp.htm. pp. 1-3. date unknown but before the filing date of this application.
Vaia, Richard A.; Vasudevan, S.; Krawlec, Wlodzimierz; Scanlon, Lawrence G.; Giannelis, Emmanuel P. New Polymer Electrolyte Nanocomposites: Milt Intercalation of Poly (ethylene oxide) in Mica-Type Silicates. Advanced Materials. vol. 7 No. 2. 1995. pp. 154-156.
Levy, Rachel; Francis, C.W. "Interlayer Adsorption of Polyvinylpyrrolidone on Montmorillonite". Journal of Colloid and Interface Sience. vol. 50 No. 3. Mar. 1975. pp. 442-450.
Greenland, D.J.; "Adsorption of Polyvinyl Alcohols by Montmorillonite". Journal of Colloid Science. vol. 18. 1963. pp. 647-664.

*Primary Examiner*—Carlos A. Azpuru
(74) *Attorney, Agent, or Firm*—Mayer & Williams PC; David B. Bonham

(57) ABSTRACT

A medical article comprising: (a) a therapeutic agent; and (b) a release region comprising (i) a polymer and (ii) a filler comprising inorganic platelet particles. Upon placement of such a medical article at a position on or within a patient, the release region regulates the rate of release of the therapeutic agent from the medical article to the patient. An example of a filler is one comprising inorganic platelet particles. Examples of medical articles include, for instance, drug delivery patches, and implantable or insertable medical devices. Also described are methods of releasing a therapeutic agent to a patient using such medical articles, and methods of making such medical articles.

24 Claims, 1 Drawing Sheet

POLYMER-FILLER COMPOSITES FOR CONTROLLED DELIVERY OF THERAPEUTIC AGENTS FROM MEDICAL ARTICLES

FIELD OF THE INVENTION

The present invention relates to medical articles which are useful for the controlled delivery of therapeutic agents.

BACKGROUND OF THE INVENTION

Medical articles are frequently used for delivery of therapeutic agents. For example, an implantable or insertable medical device, such as a stent or catheter, may be provided with a polymer matrix coating layer that contains a therapeutic agent. Once the medical device is placed at a desired location within a patient, the therapeutic agent is released from the polymer matrix and into the patient, thereby achieving a desired therapeutic outcome.

Techniques for changing the release rate of the therapeutic agent from the polymer matrix coating layer include the following: (a) changing the therapeutic agent loading level, (b) adding one or more additional polymers to the polymer matrix, for example, to alter the hydrophilic/hydrophobic balance of the matrix, (c) disposing one or more polymeric barrier layers over the therapeutic-agent-containing region, and (d) where a biodegradable polymer matrix is employed, changing the degradation properties of the polymer.

As is well known, silicates such as clay belong to a family of minerals that have a layered structure. The atoms within a given layer are tightly bound together, but the forces between adjacent layers are relatively weak. As a result, it is possible to separate the layers form one another. Under proper conditions, a single atomic layer can be separated from neighboring layers. Consequently, preparations are presently commercially available which contain molecularly thin platelet particles. These platelet particles are typically on the order of about 10 Angstroms (or 1 nm) in thickness, and on the order of 0.1 to 10 microns in lateral dimension. The use of such platelet particles to reduce the permeability of polymers has been described in U.S. Pat. No. 6,232,389, with regard to coated elastomeric articles, such as sports balls and other inflatable articles.

SUMMARY OF THE INVENTION

The present invention is directed to novel release regions for controlling the rate at which therapeutic agents are released from medical articles.

According to one aspect of the present invention, a medical article (for instance, a drug delivery patch, an implantable or insertable medical device, among others) is provided which comprises the following: (a) a therapeutic agent; and (b) a release region comprising (i) a polymer and (ii) a filler comprising inorganic platelet particles (for instance, exfoliated silicate platelet particles, among others). Upon placement of the medical article at a position on or within a patient, the release region regulates the rate of release of the therapeutic agent from the medical article to the patient.

Another aspect of the present invention is directed to methods of providing such medical articles. Such methods comprise: (a) providing a substrate (e.g., a releasable template or a medical article substrate); (b) contacting the substrate with a release-region-forming fluid, which comprises the following: (i) a polymer, (ii) inorganic platelet particles, and (iii) a fluid diluent; and (b) drying the release-region-forming fluid to form the release layer.

Yet another aspect of the present invention is directed to methods of releasing a therapeutic agent into a patient by contacting (e.g., adhering, implanting, inserting, and so forth) the above medical articles with the patient.

An advantage of the present invention is that medical articles can be provided, which regulate the release of therapeutic agent from a medical article to a patient.

Another advantage of the present invention is that medical articles can be provided in which the release of a therapeutic agent is substantially delayed due to the presence of inorganic platelet particles in a polymeric release region.

These and other aspects, embodiments and advantages of the present invention will become immediately apparent to those of ordinary skill in the art upon review of the Detailed Description and claims to follow.

DETAILED DESCRIPTION OF THE INVENTION

Figure 1:
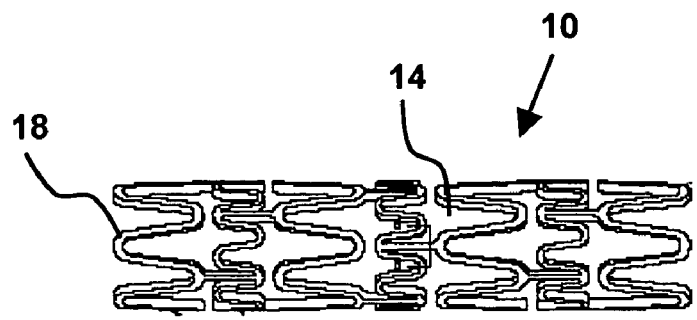
FIG. 1 is a schematic diagram of a stent having a release layer in accordance with an embodiment of the invention.

According to an aspect of the present invention, a medical article is provided, which comprises: (a) a release region and (b) a therapeutic agent. The release region further comprises (i) a polymer and (ii) a filler, which comprises inorganic platelet particles. The release region regulates the rate at which the therapeutic agent is released from the medical article upon placement of the medical article at a position on or within a patient. In general, the presence of the inorganic platelet particles results in a reduced release rate for the therapeutic agent, relative to an analogous release region in which the inorganic platelet particles are absent. In certain embodiments, the release region comprises the therapeutic agent. In certain embodiments, the release region is disposed over a region that comprises the therapeutic agent.

Release regions for use in accordance with the present invention include carrier regions and barrier regions. By "carrier region" is meant a release region which further comprises a therapeutic agent and from which the therapeutic agent is released. For example, in some embodiments, the carrier region is disposed over all or a portion of a medical article substrate. In other embodiments, the carrier region constitutes the entirety of the medical article.

By "barrier region" is meant a region which is disposed between a source of therapeutic agent and a site of intended release, and which controls the rate at which therapeutic agent is released. For example, in some embodiments, the medical article consists of a barrier region that surrounds a source of therapeutic agent. In other embodiments, the carrier region is disposed over a source of therapeutic agent, which is in turn disposed over all or a portion of a medical article substrate.

In various embodiments, release regions for use in accordance with the present invention are in the form of a release layer, which covers all or a part of a medical article substrate. As used herein a "layer" of a given material is a region of that material whose thickness is small compared to both its length and width (e.g., the length and width dimensions may both be at least 5, 10, 20, 50, 100 or more times the thickness dimension). As used herein a layer need not be planar, for example, taking on the contours of an underlying substrate. Layers can be discontinuous (e.g., patterned). Terms such as "film," "layer" and "coating" may be used interchangeably herein.

Medical articles for use in conjunction with the present invention include any medical article for which controlled release of a therapeutic agent is desired. Examples of medical articles include patches for delivery of therapeutic agent to intact skin, broken skin (including wounds), and surgical sites.

Examples of medical articles also include implantable or insertable medical devices, for example, catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, electrodes, heart valves, circulation pumps, biopsy devices, and any other coated substrate (which can comprise, for example, glass, metal, polymer, ceramic and combinations thereof) that is implanted or inserted into the body.

The medical articles of the present invention include medical articles that are used for either systemic treatment or for the localized treatment of any mammalian tissue or organ. Non-limiting examples are tumors; organs including the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; dermal tissue; cartilage; and bone.

As used herein, "treatment" refers to the prevention of a disease or condition, the reduction or elimination of symptoms associated with a disease or condition, or the substantial or complete elimination a disease or condition. Preferred subjects are mammalian subjects and more preferably human subjects.

Specific examples of medical articles for use in conjunction with the present invention include vascular stents, which deliver therapeutic agent into the vasculature for the treatment of restenosis. In these embodiments, the release region is typically provided over all or a portion of a stent substrate, and is typically in the form of a carrier layer (in which case therapeutic agent is disposed within the release layer) or a barrier layer (in which case the release layer is disposed over a therapeutic-agent containing region).

FIG. 1 illustrates a vascular stent 10, in accordance with an embodiment of the present invention. Stent 10 can be, for example, a coronary stent, sized to fit in the blood vessel of a patient, which is formed from a plurality of structural elements 18. The construction of each stent 10 permits the stent 10 to be introduced into the vascular system in a collapsed configuration, minimizing the diameter of the stent 10. Stent 10 can then expand to an expanded position at the desired location within the blood vessel of the patient. The structural elements 18 of stent 10 form a frame, such as tubular shape, permitting the stent 10 to self-expand or to expand to the desired shape after an expansive force is applied, for example, by the expansion of a balloon within the stent. The structural elements 18 of stent 10 form windows 14 such that the stent 10 does not have a continuous outer shell. Windows 14 are generally present in most stent configurations, although the specific details of the shape of structural elements 18 and the construction of stent 10 can vary.

Figure 2A:
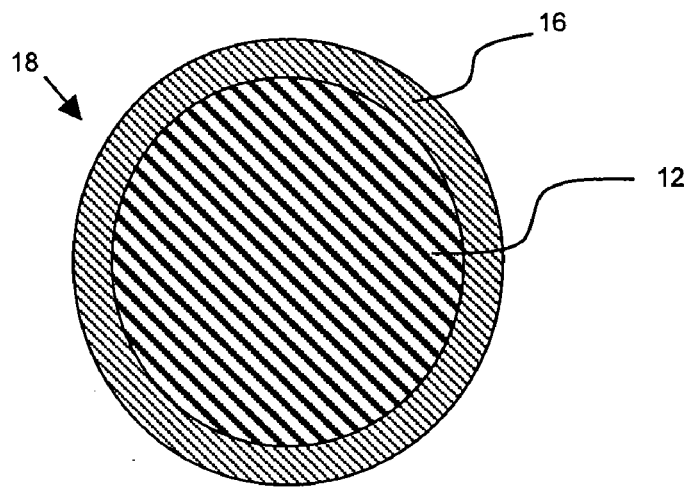
FIGS. 2A and 2B are schematic cross-sectional illustrations of a structural element of a stent like that of FIG. 1, in accordance with two alternate embodiments of the invention.
Figure 2B:
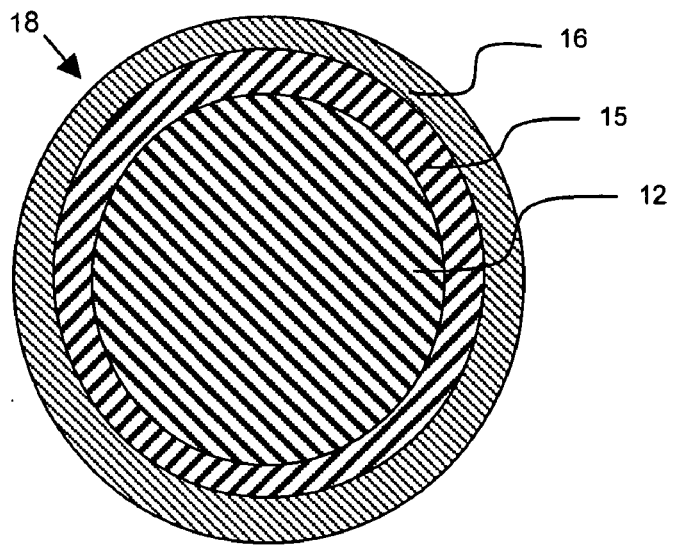

A release layer is applied on the surface of the stent 10. For example, FIGS. 2A and 2B are schematic cross-sectional views of a structural element 18 of a stent like that of FIG. 1, in accordance with two alternate embodiments of the invention. In FIG. 2A, the release layer 16 is a carrier layer (containing polymer, filler and therapeutic agent), which is directly adjacent the underlying structural member 12. In FIG. 2B, the release layer 16 is a barrier layer (containing polymer and filler), which is adjacent a therapeutic-agent-containing layer 15. In turn, the therapeutic-agent-containing layer 15 is adjacent the underlying structural member 12. In either case, the therapeutic agent is released in a controlled manner after introduction of the stent 10 into the body of the patient.

Medical devices having sustained release profiles are beneficial in many cases. By "sustained release profile" is meant a release profile in which less than 25% of the total release from the medical device that occurs over the course of implantation/insertion in the body occurs after 1 day (or in some embodiments after 2, 4, 8, 16, 32, 64, 128 or even more days) of administration. Conversely, this means that more than 75% of the total release from the medical device will occur after the device has been implanted/inserted for the same period.

The release characteristics that are ultimately of interest are, of course, the release characteristics within the subject, for example, within a mammalian subject. However, it is well known in the art to test the release characteristics within an experimental system that gives an indication of the actual release characteristics within the subject. For example, aqueous buffer systems such as Tris buffer or phosphate buffered saline are commonly used for testing release of therapeutic agents from vascular devices.

As noted above, the release regions of the present invention comprise (i) a polymer and (ii) a filler, which further comprises inorganic platelet particles.

The inorganic platelet particles for use in the filler are typically those that are extracted from inorganic layered silicates, for instance, silicate clays (which are in the form of a plurality of adjacent, bound layers). The individual layers of such silicate materials are typically 100 Å or less in thickness. Examples of layered silicates include bentonite, vermiculite, montmorillonite, nontronite, beidellite, volkonskoite, hectorite, saponite, laponite, sauconite, magadiite, kenyaite, aliettite, swinefordite, yakhontovite, stevensite, ledikite, other smectite group clays, and mixtures thereof.

Preferably at least a portion of the inorganic platelet particles are exfoliated. For inorganic layered materials such as inorganic layered silicates, "exfoliation" is defined as the complete separation of an individual layer from a particle of the inorganic layered material (e.g., an inorganic layered silicate particle), such that the individual layer is surrounded by another medium, for example, a polymer in the case of the release regions of the present invention, or a dispersion fluid, such as an aqueous or non-aqueous medium, in the case of the release-region-forming fluids described below.

A variety of polymers are available for use in the release regions of the present invention. For example, the polymer may be a homopolymer or a copolymer (including alternating, random and block copolymers), may be cyclic, linear or branched (e.g., polymers having star, comb or dendritic architecture), may be natural or synthetic, may be thermoplastic or thermosetting. Polymers for the practice of the invention may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Elastomeric polymers are particularly beneficial. Among the preferred elastomeric polymers are (a) polyolefin polymers, for example, butyl containing polymers such as polyisobutylene, (b) polyolefin copolymers, for example, polyolefin-polyvinylaromatic copolymers such as polyisobutylene-polystyrene copolymers, poly(butadiene/butylene)-polystyrene copolymers, poly(ethylene/butylene)-polystyrene copolymers, and polybutadiene-polystyrene copolymers; (c) silicone polymers and copolymers; and (d) acrylic acid polymers and copolymers; as well as blends thereof. Specific examples of polyolefin-polyvinylaromatic copolymers include polyolefin-polyvinylaromatic diblock copolymers and polyvinylaromatic-polyolefin-polyvinylaromatic triblock copolymers, such as a polystyrene-polyethylene/butylene-polystyrene (SEBS) triblock copolymer, available as Kraton® and polystyrene-polyisobutylene-polystyrene (SIBS) triblock copolymers, which are described, for example, in U.S. Pat. Nos. 5,741,331, 4,946,899 and 6,545,097, each of which is hereby incorporated by reference in its entirety. Additional polyolefin-polyvinylaromatic copolymers are set forth in the prior paragraph.

In various beneficial embodiments of the invention, release regions are created using a release-region-forming fluid that comprises the following components: (a) a polymer, (b) a filler comprising inorganic platelet particles, (c) a fluid diluent (e.g., water, organic solvent, or a mixture thereof), and (d) various optional agents (e.g., therapeutic agents, surfactants, contrast agents, radioisotopes, etc.).

Examples of fluid diluents for use in conjunction with the release-region-forming fluid include water, organic solvents such as hexane, heptane, toluene, 1 methyl-2-pyrrolidinone, cyclohexanone, ethanol, methanol, and chloroform, as well as combinations of the same.

Polymer(s) for use in conjunction with the release-region-forming fluid may be selected, for example, from those listed above and may be present, for example, in dissolved (e.g., solution) or dispersed (e.g., latex, pseudolatex) form. In certain beneficial embodiments, a polymer latex is utilized. Numerous polymer latexes are known including various butyl and other polymer based latexes. Commercially available latexes frequently contain ionic surfactant(s) which stabilize the latex and may also affect the properties of the release region.

Fillers for use in conjunction with the release-region-forming fluid include the exfoliated inorganic platelet particles discussed above. Typically, the exfoliated inorganic platelet particles are exfoliated silicate platelet particles. The exfoliated inorganic platelet particles beneficially have an aspect ratio of at least 25, more beneficially at least 100, even more beneficially at least 1000 or 10,000 or more. The term "aspect ratio" is an inherent characteristic of platelet particles. Aspect ratio is the minimum width of a platelet particle divided by its thickness.

For example, exfoliated vermiculite is a desirable filler material due to its very high aspect ratio. Preparations are available, such as MicroLite® 963++ aqueous vermiculite dispersion (W. R. Grace & Co.), in which dispersed vermiculite platelet particles have an average width of 10-30 microns. The platelet particles are largely exfoliated in the aqueous dispersion, and their thickness is 1-2 nm. Hence, the aspect ratio of the platelet particles in the aqueous dispersion commonly averages between 10,000 and 30,000. Other less exfoliated grades of MicroLite® vermiculite (e.g., grades 963, 923, and 903) are also available. Aspect ratio can be determined by a number of techniques including microscopy. Many platelet particles may reassemble during the formation of the release region, thus reducing the aspect ratio of many of the platelet particles relative to their aspect ratio in aqueous dispersion. However, the release regions of the present invention nevertheless retain platelet particles in well-dispersed form, in general, promoting a reduction in the release rate of the therapeutic agent.

In addition to diluent, filler and polymer, the release-region-forming fluid can also include one or more therapeutic agents (e.g., where the release region is a carrier region), which can be selected from the therapeutic agents set forth below, among others. Moreover, the in certain embodiments, the release-region-forming fluid can also optionally include: (a) one or more suitable surfactants to reduce surface tension and/or one or more suitable thickeners to adjust viscosity, as described, for example, in U.S. Pat. No. 6,232,389, the disclosure of which is incorporated by reference, and (b) one or more contrast agents or radioisotopes.

In certain beneficial embodiments of the invention, the release-region-forming fluid has a solids content between about 1% and about 30% solids, for instance, between about 5% to about 17% solids. Examples of polymer-to-filler ratios include, for instance, ratios of between about 20:1 to about 1:1.

Once a suitable release-region-forming fluid is provided, it can be used to form release regions in accordance with the present invention using a variety of techniques.

Beneficial techniques include, for example, casting techniques, spin coating techniques, web coating techniques, spraying techniques, roll and brush coating techniques, dipping techniques, techniques involving coating via mechanical suspension such as air suspension, ink jet techniques, electrostatic techniques, and combinations of these processes.

In some of these techniques, the release-region-forming fluid is applied to a substrate in order to form the release region. For example, in some embodiments, the substrate is all or a portion of a medical article (e.g., an implantable or insertable medical device) to which the release region is applied. In some embodiments, the substrate is a template (including sheets, tubes, molds and other forms) from which the release region is removed after formation.

In other techniques, for example, fiber forming techniques, the release region is formed without the aid of a substrate.

Where appropriate, techniques such as those listed above can be repeated or combined to build up a release region to a desired thickness. The thickness of the release region can be varied in other ways as well. For example, where the release region is formed by spraying, thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent is included in the release-region-forming fluid in some embodiments and hence co-established with the carrier region. In other embodiments, the therapeutic agent is introduced into a previously formed release region. For example, the therapeutic agent can be dissolved within a solvent, and the resulting solution contacted with the previously formed release region using, for example, one or more of the application techniques described above (e.g., dipping, spraying, etc.) to form a carrier region.

As previously noted, barrier regions are regions which are provided between a therapeutic-agent-containing region and a site of intended release (commonly an outer surface of the medical article). Hence, in various embodiments, a barrier region in accordance with the present invention is formed over a previously formed therapeutic-agent-containing region. In some instances, the therapeutic-agent-containing region comprises one or more polymers, which can be selected, for example, from the polymers described elsewhere in this application. In some instances, the therapeutic-agent-containing region is established without a polymer. In either case, the therapeutic-agent-containing region can be formed, for example, by dissolving or dispersing therapeutic agent (an any other component(s) of the of the therapeutic-agent-containing region) in a fluid, and applying the resulting solution/dispersion to a substrate using, for instance, the application techniques described above (e.g., dipping, spraying, etc.).

Where the release region is created using a release-region-forming fluid, the diluent is removed after application, for example, by drying at room or elevated (e.g., 50° C.) temperature, while under ambient pressure or under vacuum.

In some embodiments, the filler comprising the inorganic platelet particles is provided within a polymer melt. For example, in some embodiments, a hydrophilic polymer is utilized as the carrier polymer, which is capable of exfoliating the platelet particles in the melt phase. In some embodiments, platelet particles are exfoliated within a hydrophobic polymer melt by rendering the particles them more hydrophobic. For example, it is known to render layered silicates more hydrophobic by exchanging endogenous inorganic cations found within the silicate particles with one or more species having a positive charge and having a hydrophobic domain. Examples of such species include alkylammonium ions, for instance, tertiary and quaternary alkylammonium ions, such as trimethyl ammonium ions and hexadecyltrimethylammonium (HDTMA) ions. Alternatively, species such as those described in U.S. Pat. Nos. 6,057,396 and 6,083,559, the disclosures of which are hereby incorporated by reference, can be introduced into layered silicates, allowing them to be exfoliated. These species include: (a) organic compounds comprising an alkyl radical of at least six carbons and a polar functionality, for example, alcohols and polyalcohols, carbonyl compounds (including carboxylic acids, polycarboxylic acids, and salts thereof), aldehydes, ketones, amines, amides, ethers, esters, lactams, lactones, anhydrides, alkyl nitrites, n-alkyl halides and pyridines, and (b) organic compounds having hydroxyl, polyhydroxyl, and/or aromatic functionality, for example, aliphatic alcohols, aromatic alcohols, aryl substituted aliphatic alcohols, alkyl substituted aromatic alcohols, and polyhydric alcohols.

Once a melt is established that contains polymer, filler and optional agents (e.g., therapeutic agents, contrast agents, radioisotopes, etc.), a release region in accordance with the present invention can be formed using various thermoplastic processing techniques, including molding techniques (for example, injection molding, rotational molding, and so forth), extrusion techniques (for example, extrusion, co-extrusion, multi-layer extrusion, multi-lumen extrusion, and so forth) and casting techniques, among others.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. The therapeutic agent can be selected from suitable members of the lists of therapeutic agents to follow.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines and (r) hormones.

Some exemplary non-genetic therapeutic agents include paclitaxel, sirolimus, everolimus, tacrolimus, cladribine, halofuginone·HBr, dexamethasone, estradiol, ABT-578 (Abbott Laboratories), trapidil, liprostin, Actinomcin D, Resten-NG, Ap-17, abciximab, clopidogrel and Ridogrel.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP 1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including $\alpha$-antagonists such as prazosin and bunazosine, $\beta$-antagonists such as propranolol and $\alpha/\beta$-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and $\beta$-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-$\beta$ pathway agents such as polyanionic agents (heparin, fucoidin), decorin, and TGF-$\beta$ antibodies, EGF pathway agents such as EGF antibodies, receptor antagonists and chimeric fusion proteins, TNF-$\alpha$ pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents are also disclosed in U.S. Pat. No. 5,733,925 assigned to NeoRx Corporation, the entire disclosure of which is incorporated by reference.

A wide range of therapeutic agent loadings can be used in connection with the release regions of the present invention, with the therapeutically effective amount being readily determined by those of ordinary skill in the art and ultimately depending, for example, upon the condition to be treated, the age, sex and condition of the patient, the nature of the therapeutic agent, the nature of the release region, the nature of the medical article, and so forth.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical article comprising:
   (a) a therapeutic agent; and
   (b) a release region comprising (i) a polymer and (ii) a filler comprising inorganic platelet particles, said release region regulating the rate of release of the therapeutic agent from the medical article upon placement of the medical article at a position on or within a patient, wherein said release region is selected from a release region that comprises said therapeutic agent and a release region that is disposed over a region that comprises said therapeutic agent.

2. The medical article of claim 1, wherein said release region comprises said therapeutic agent.

3. The medical article of claim 1, wherein said release region is disposed over a region that comprises said therapeutic agent.

4. The medical article of claim 1, wherein said release region is disposed over at least a portion of a substrate.

5. The medical article of claim 4, wherein said release region comprises said therapeutic agent.

6. The medical article of claim 4, wherein said release region is disposed over a layer that comprises said therapeutic agent, which is further disposed over said substrate.

7. The medical article of claim 1, wherein said medical article is adapted for implantation or insertion into a human body.

8. The medical article of claim 7, wherein said medical article is adapted for implantation or insertion into the vasculature.

9. The medical article of claim 7, wherein said medical article is selected from a catheter, a guide wire, a balloon, a filter, a stent, a stern graft, a vascular graft, a vascular patch, a shunt, and an intraluminal paving system.

10. The medical article of claim 7, wherein said medical article is adapted for implantation or insertion into the esophagus, trachea, colon, biliary tract, urinary tract, prostate or brain.

11. The medical article of claim 1, wherein said therapeutic agent is selected from an anti-thrombotic agent, an anti-proliferative agent, an anti-inflammatory agent, an anti-migratory agent, an agent affecting extracellular matrix production and organization, an antineoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms, or a combination of the same.

12. The medical article of claim 1, wherein said wherein said filler comprises inorganic platelet particles having an aspect ratio greater than 100.

13. The medical article of claim 1, wherein said wherein said filler comprises inorganic platelet particles having an aspect ratio greater than 1000.

14. The medical article of claim 1, wherein said wherein said filler comprises exfoliated silicate platelet particles.

15. The medical article of claim 1, wherein said filler comprises exfoliated silicate platelet particles selected from exfoliated bentonite platelet particles, exfoliated vermiculite platelet particles, exfoliated montmuorillonite platelet particles, exfoliated nontronite platelet particles, exfoliated beidellite platelet particles, exfoliated volkonskoite platelet particles, exfoliated hectorite platelet particles, exfoliated saponite platelet particles, exfoliated laponite platelet particles, exfoliated sauconite platelet particles, exfoliated magadiite platelet particles, exfoliated kenyaite platelet particles, exfoliated ledikite platelet particles, and mixtures thereof.

16. The medical article of claim 1, wherein said filler comprises exfoliated vermiculite platelet particles.

17. The medical article of claim 1, wherein said polymer comprises a poly(olefin) segment.

18. The medical article of claim 17, wherein said polymer is a poly(olefin) homopolymer.

19. The medical article of claim 17, wherein said polymer is a block copolymer comprising a poly(alkylene) segment.

20. The medical article of claim 1, wherein said polymer comprises a poly(vinyl aromatic) segment.

21. The medical article of claim 20, wherein said polymer is a block copolymer comprising a poly(vinyl aromatic) segment.

22. The medical article of claim 1, wherein said polymer is a block copolymer comprising a poly(alkylene) segment and a poly(styrene) segment.

23. The medical article of claim 22, wherein said polymer is a block copolymer comprising a poly(isobutylene) segment and a poly(styrene) segment.

24. The medical article of claim 23, wherein said block polymer is a polystyrene-polyisobutylene-polystyrene triblock copolymer.

* * * * *

UNITED STATES PATENT AND TRADEMARK OFFICE
CERTIFICATE OF CORRECTION

PATENT NO.         : 7,537,781 B2
APPLICATION NO. : 10/777801
DATED              : May 26, 2009
INVENTOR(S)        : Robert E. Richard Page 1 of 1

It is certified that error appears in the above-identified patent and that said Letters Patent is hereby corrected as shown below:

Specification, Col. 1, line 33, after "layer", change "form" to --from--.

Specification, Col. 4, line 57, after "and", change last word "hydoxy-" to --hydroxy- --.

Specification, Col. 6, line 12, after "toluene,", change "1 methyl-2-pyrrolidinone," to --1-methyl-2-pyrrolidinone--.

Specification, Col. 6, line 55, after "Moreover,", delete "the".

Specification, Col. 7, line 49, after "agent", change "(an" to --(and--.

Specification, Col. 7, line 50, after "component(s)", delete "of the".

Specification, Col. 7, line 63, after "particles", delete "them".

Specification, Col. 9, line 38, after "PVP,", change "SP 1017" to --SP1017--.

Claim 9, Col. 11, line 52, before "graft", change "stern" to --stent--.

Claim 12, Col. 12, line 11, after "claim 1," delete "wherein said".

Claim 13, Col. 12, line 14, after "claim 1," delete "wherein said".

Claim 14, Col. 12, line 17, after "claim 1," delete "wherein said".

Signed and Sealed this

Fifteenth Day of September, 2009

David J. Kappos
*Director of the United States Patent and Trademark Office*